(12) United States Patent
Richard

(10) Patent No.: US 7,510,703 B2
(45) Date of Patent: Mar. 31, 2009

(54) UV-PHOTOPROTECTING/SUNSCREEN COMPOSITIONS COMPRISING SILANE/SILOXANE DERIVATIVES OF MEROCYANINE SULFONES

(75) Inventor: Herve Richard, Villepinte (FR)

(73) Assignee: L'Oreal, Paris (FR)

( * ) Notice: Subject to any disclaimer, the term of this patent is extended or adjusted under 35 U.S.C. 154(b) by 176 days.

(21) Appl. No.: 11/725,485

(22) Filed: Mar. 20, 2007

(65) Prior Publication Data

US 2007/0224147 A1    Sep. 27, 2007

Related U.S. Application Data

(63) Continuation of application No. PCT/FR2005/002129, filed as application No. 60/613,967 on Sep. 29, 2004.

(30) Foreign Application Priority Data

Sep. 20, 2004 (FR) .................... 04 52093

(51) Int. Cl.
    *C03C 25/24*     (2006.01)
    *A61K 8/00*     (2006.01)
    *A61K 8/18*     (2006.01)
    *A61Q 17/04*     (2006.01)
    *C07F 7/18*     (2006.01)

(52) U.S. Cl. .................. 424/59; 65/448; 424/70.9; 556/9

(58) Field of Classification Search .................. None
See application file for complete search history.

(56) References Cited

U.S. PATENT DOCUMENTS

| | | | |
|---|---|---|---|
| 4,195,999 | A | 4/1980 | Adachi et al. |
| 7,138,108 | B2 | 11/2006 | Richard et al. |
| 2002/0081271 | A1 | 6/2002 | Martin et al. |
| 2004/0059119 | A1 | 3/2004 | Candau |

FOREIGN PATENT DOCUMENTS

EP      1371654 B1      12/2003

WO      WO 2004/006878 A1      1/2004

OTHER PUBLICATIONS

International Search Report corresponding to PCT/FR 2005/002127, issued on Feb. 9, 2006, 4 pages.

*Primary Examiner*—Johann R Richter
*Assistant Examiner*—Luke E Karpinski
(74) *Attorney, Agent, or Firm*—Buchanan, Ingersoll & Rooney P.C.

(57) ABSTRACT

Topically applicable cosmetic compositions useful for the UV-A photoprotection of the skin and/or hair contain thus effective amounts of at least one silane, siloxane or polysiloxane merocyanine sulfone having at least one of the structural formulae (1), (2) and (3) below:

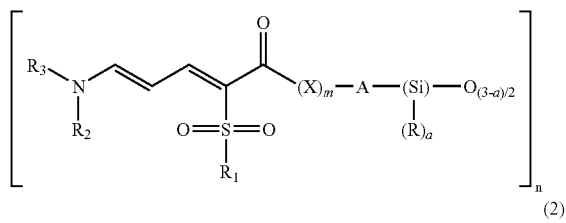

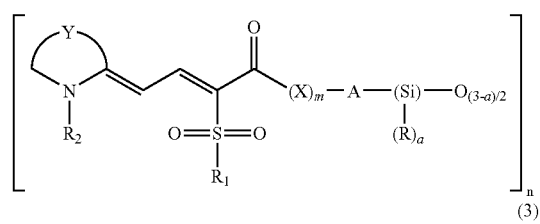

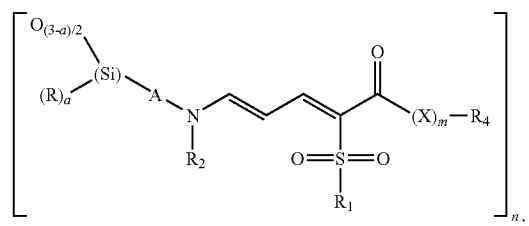

28 Claims, No Drawings

UV-PHOTOPROTECTING/SUNSCREEN COMPOSITIONS COMPRISING SILANE/SILOXANE DERIVATIVES OF MEROCYANINE SULFONES

CROSS-REFERENCE TO PRIORITY/PCT/PROVISIONAL APPLICATIONS

This application claims priority under 35 U.S.C. § 119 of FR 04/52093, filed Sep. 20, 2004, and of Provisional Application No. 60/613,967, filed Sep. 29, 2004, and is a continuation of PCT/FR 2005/002129 filed Aug. 24, 2005 and designating the United States, published in the French language as WO 2006/032741 A1 on Mar. 30, 2006 (the title and abstract were also published in English), each hereby expressly incorporated by reference in its entirety and each assigned to the assignee hereof.

BACKGROUND OF THE INVENTION

1. Technical Field of the Invention

The present invention relates to novel silane, siloxane or polysiloxane derivatives of merocyanine sulfones and to their formulation into cosmetics as "long" UV-A filters.

The present invention also relates to cosmetic compositions for topical application, in particular useful for the photoprotection of skin and/or hair, comprising an effective quantity of at least one silane, siloxane or polysiloxane derivative of merocyanine sulfone or a mixture of such derivatives.

2. Description of Background and/or Related and/or Prior Art

Radiation with wavelengths in the range 280 nm [nanometer] to 400 nm is known to brown human skin, and radiation with wavelengths in the range 280 nm to 320 nm, known as UV-B radiation, causes erythemas and burns to the skin which can interfere with the development of a natural tan.

UV-A radiation with wavelengths in the range 320 nm to 400 nm is also known to cause the skin to brown, but is capable of inducing an alteration in the skin, in particular in the case of sensitive skin and/or skin continuously exposed to solar radiation. In particular, UV-A radiation causes loss of skin elasticity and the appearance of wrinkles, resulting in premature aging of the skin. It promotes triggering of the erythematous reaction or amplifies that reaction in certain individuals and may even be at the source of phototoxic or photoallergic reactions. Thus, for aesthetic and cosmetic reasons, such as preserving the natural elasticity of the skin, more and more individuals wish to control the effect of UV-A radiation on their skin. The term "sun protection factor" means the ratio of the irradiation period necessary to reach the erythematogenic threshold in the presence of a test filter to the irradiation period necessary to reach that same threshold in the absence of a filter.

A large number of organic compounds suited to protect the skin against UV-A and/or UV-B radiation have been proposed to this art.

The majority of these are aromatic compounds absorbing UV radiation in the range 280 nm to 315 nm or in the range 315 nm to 400 nm and beyond, or across both of those zones. They are usually formulated into sunscreen compositions which are in the form of oil-in-water emulsions or water-in-oil emulsions. The organic filters, which are generally lipophilic or hydrophilic, are present in a dissolved state in one or the other of those phases in quantities appropriate for obtaining the desired sun protection factor (SPF).

In addition to their solar radiation filtration capability, desirable photoprotective compounds must also have other good cosmetic properties, good solubility in the usual solvents, in particular in fatty substances such as oils or fats, and good resistance to water and perspiration (persistance), as well as very good photostability.

Compounds which have been recommended for that purpose which are exemplary include a particularly interesting family of filters constituted by carbonaceous merocyanine derivatives described in U.S. Pat. No. 4,195,999 or WO-A-2004/006878. Those compounds have very good long UV-A filtering properties but have poor solubility in the usual organic solvents and in particular in fatty substances such as oils, and unsatisfactory photostability for certain merocyanine families.

SUMMARY OF THE INVENTION

A novel family of silane, siloxane or polysiloxane derivatives of merocyanine sulfones has now been developed having good long UV-A filtering properties, very good solubility in the usual organic solvents and excellent cosmetic properties compared with the merocyanines described in WO-A-2004/006878.

The present invention thus features a novel family of silane, siloxane and polysiloxane derivatives of merocyanine sulfones having the formulae (1), (2) and (3) which will be described below in more detail.

This invention also features cosmetic or dermatological compositions useful for the photoprotection of keratinous material containing, formulated into a physiologically acceptable medium, at least one compound of formulae (1), (2) or (3).

The term "physiologically acceptable medium" means a non-toxic medium which can be topically applied to the skin, lips, hair, eyelashes, eyebrows or nails. The compositions of the invention may, in particular, constitute cosmetic or dermatological compositions.

Other aspects of the invention will become apparent from the description to follow.

DETAILED DESCRIPTION OF BEST MODE AND SPECIFIC/PREFERRED EMBODIMENTS OF THE INVENTION

The compounds of the present invention have one or another of the formulae (1), (2) or (3) below:

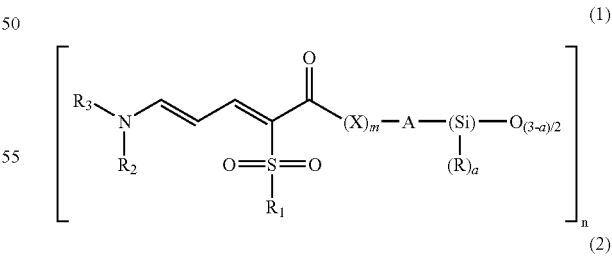

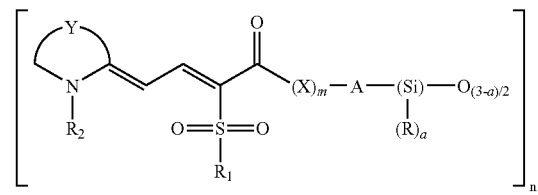

-continued

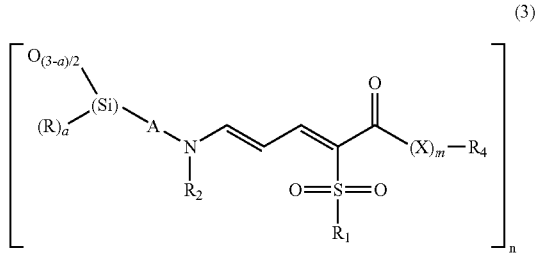
(3)

in which:

m=0 or 1;

X is —O—, —$NR_5$—, —$SO_2NH$—, wherein $R_5$ is hydrogen or a $C_1$-$C_5$ alkyl radical;

Y is a divalent $C_1$-$C_5$ alkyl radical optionally substituted with $C_1$-$C_4$ alkyl radicals and/or containing —O—, —S— atoms or with a —$NR_1$ group;

the radicals R, which may be identical or different, are each a linear or branched and optionally halogenated $C_1$-$C_{20}$ alkyl radical, a $C_6$-$C_{12}$ aryl radical or a $C_1$-$C_{10}$ alkoxy radical;

a=0 to 3;

$R_1$ is a linear or branched and optionally halogenated $C_1$-$C_{20}$ alkyl radical or a $C_6$-$C_{12}$ aryl radical;

$R_2$ and $R_3$, which may be identical or different, are each H, a $C_1$-$C_{24}$ alkyl radical, a $C_3$-$C_{10}$ cycloalkyl radical or a $C_6$-$C_{20}$ aryl radical optionally substituted with alkyl or alkoxy radicals, with the proviso that $R_2$ and $R_3$ may together form, with the nitrogen atom from which they depend, a $C_4$-$C_6$ cycle optionally interrupted by oxygen atoms or —NH—, and with the further proviso that $R_2$ and $R_3$ cannot each be a hydrogen atom;

A is a divalent radical selected from among methylene, ethylene or a group having one of the formulae (4), (5) or (6) below:

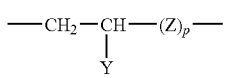
(4)

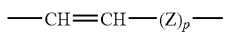
(5)

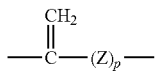
(6)

in which:

Z is a linear or branched, saturated or unsaturated $C_1$-$C_6$ alkylene radical optionally substituted with a hydroxyl radical, or a linear or branched, saturated or unsaturated $C_1$-$C_8$ alkyl radical;

W is a hydrogen atom, a hydroxyl radical or a linear or branched, saturated or unsaturated $C_1$-$C_8$ alkyl radical;

p is 0 or 1;

n=1 to 4 and when n=2, $R_1$, $R_2$, $R_3$ or $R_4$ is a divalent alkyl radical or $R_2$ and $R_3$ may together form with the nitrogen atom from which they depend, a $C_4$-$C_6$ cycle optionally interrupted by oxygen atoms or —NH—.

The compounds of formulae (1), (2) or (3) may be present in the isomeric, E,E-, E,Z- or Z,Z-forms.

In addition to structural units of formula -A-(Si)(R)$_a$(O)$_{(3-a)/2}$, the organosiloxane may contain units of formula (R)$_b$—(Si)(O)$_{(4-b)/2}$ in which:

R is as defined in formulae (1) to (3);

b=1, 2 or 3.

Preferably, the —(Si)(R)$_a$(O)$_{(3-a)/2}$ groups are represented by the formulae (7), (8) or (9) below:

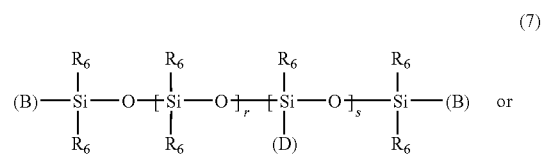
(7)

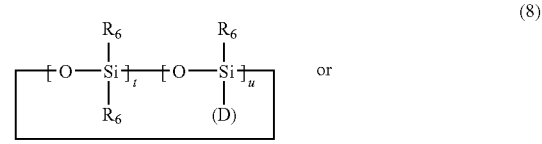
(8)

(9)

in which:

(D) is a linkage from the silicone chain and group A of the chromophores of formulae (1) to (3);

the radicals $R_6$, which may be identical or different, are each selected from among linear or branched $C_1$-$C_{30}$ alkyl, phenyl, 3,3,3-trifluoropropyl and trimethylsilyloxy radicals, at least 80% by number of the radicals $R_6$ being methyl;

the radicals (B), which may be identical or different, are each selected from among radicals $R_6$ and radical A;

r is a whole number in the range 0 to 200 inclusive and s is a whole number in the range 0 to 50 inclusive, and if s=0, at least one of the two symbols (B) designates A;

u is a whole number in the range 1 to 10 inclusive and t is a whole number in the range 0 to 10 inclusive, with the proviso that t+u is 3 or more.

In formulae (1) to (3) above, the alkyl radicals may be linear or branched, saturated or unsaturated and in particular selected from among methyl, ethyl, n-propyl, isopropyl, n-butyl, isobutyl, tert-butyl, n-amyl, isoamyl, neopentyl, n-hexyl, n-heptyl, n-octyl, 2-ethylhexyl and tert-octyl radicals. Particularly preferably, the alkyl radical is the methyl radical.

In formulae (1) to (3) above, the aryl radicals are preferably phenyl or tolyl.

More particularly, Y is a group of atoms forming an oxazolidine cycle, a pyrrolidine cycle, a thiazolidine cycle or an indoline double cycle.

The linear or cyclic diorganosiloxanes of formulas (7) or (8) according to the present invention are random polymers or oligomers preferably having at least one, and more preferably all, of the following characteristics:

$R_6$ is preferably methyl,

B is preferably methyl (in the case of linear compounds of formula (7)).

Particularly preferred examples of compounds of formula (1) include the compounds of formulae (a) to (e) below:

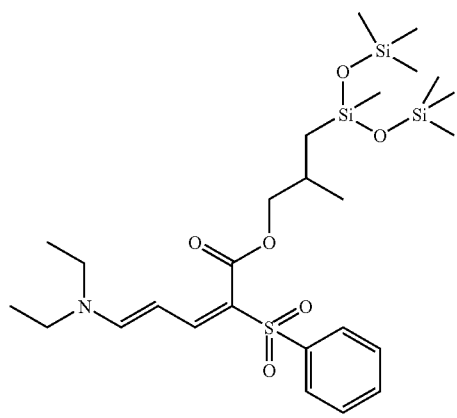
(a)
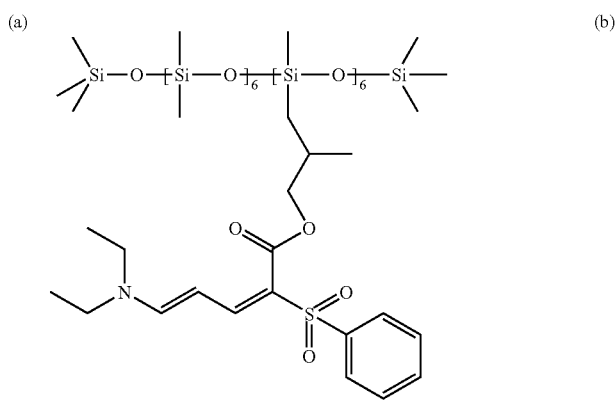
(b)
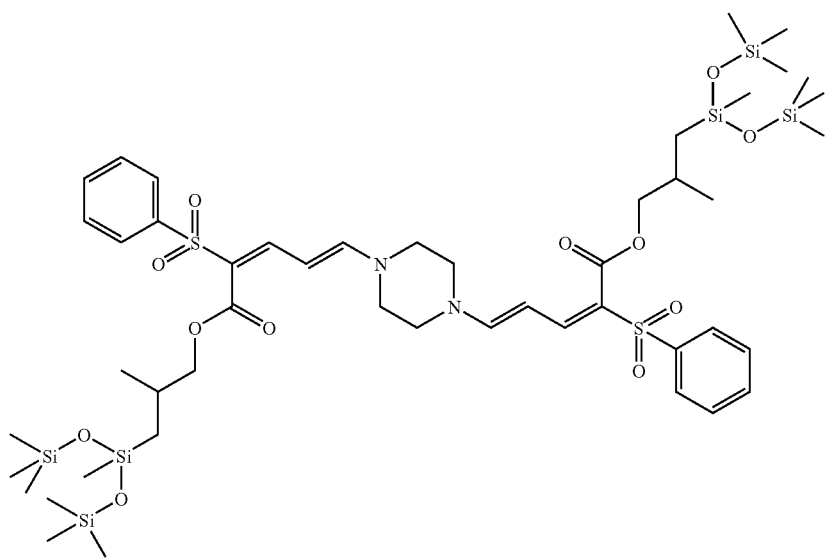
(c)
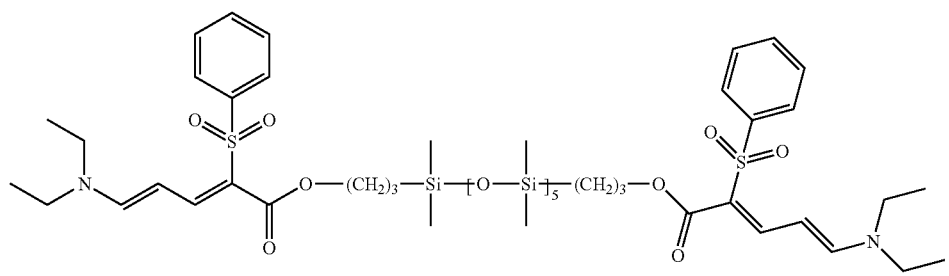
(d)

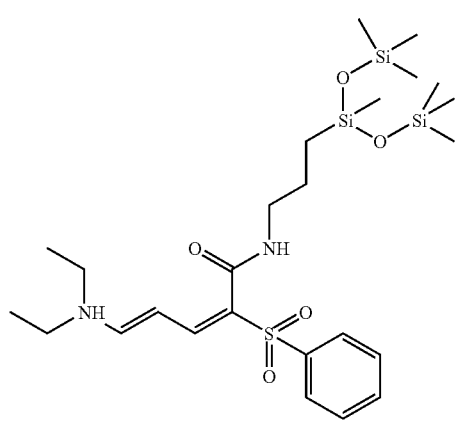
(e)
Particularly preferred examples of compounds of formula (2) include the mixture of formula (f) below:
Particularly preferred examples of compounds of formula (3) include the compounds of formulae (g) to (k) below:
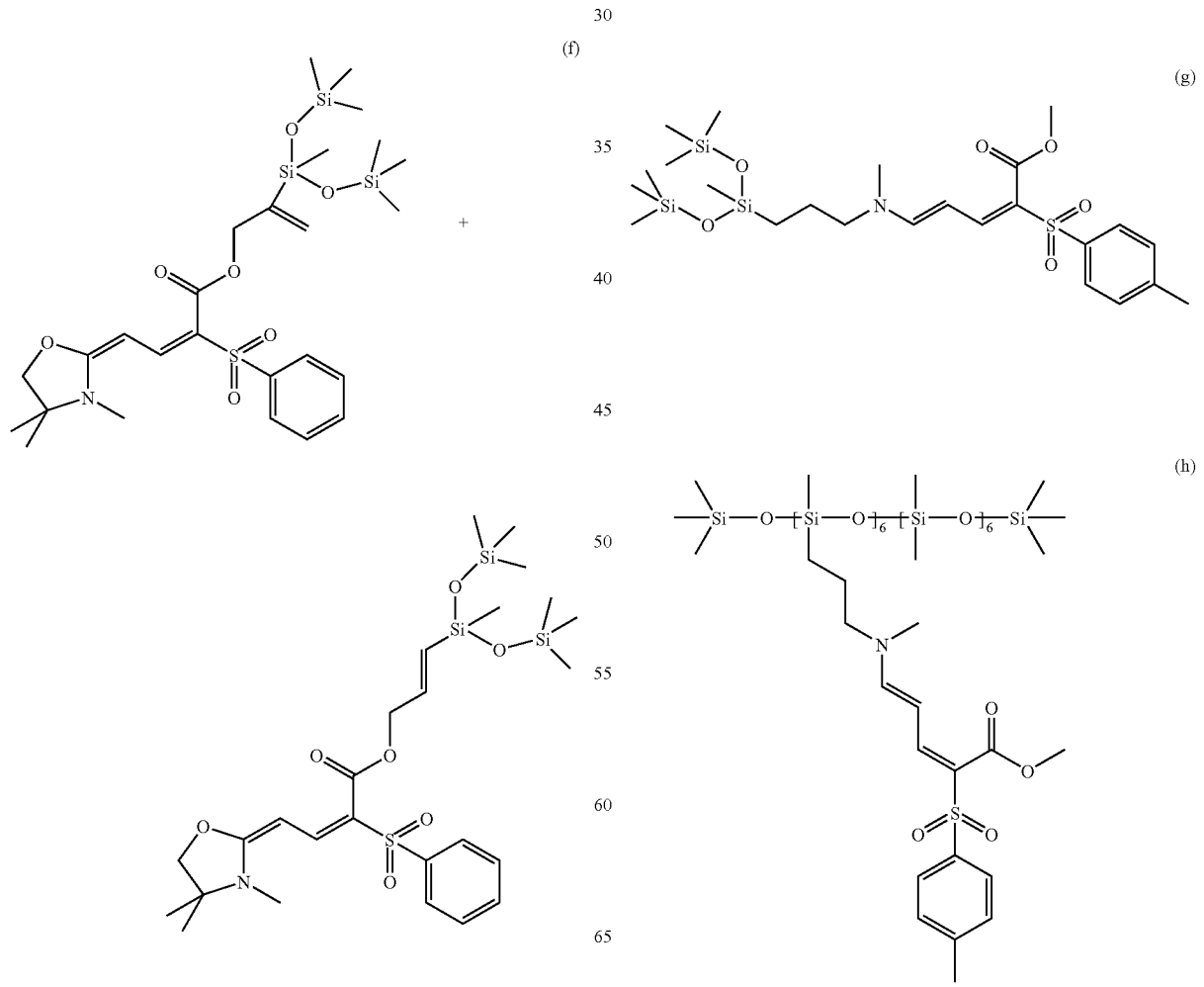

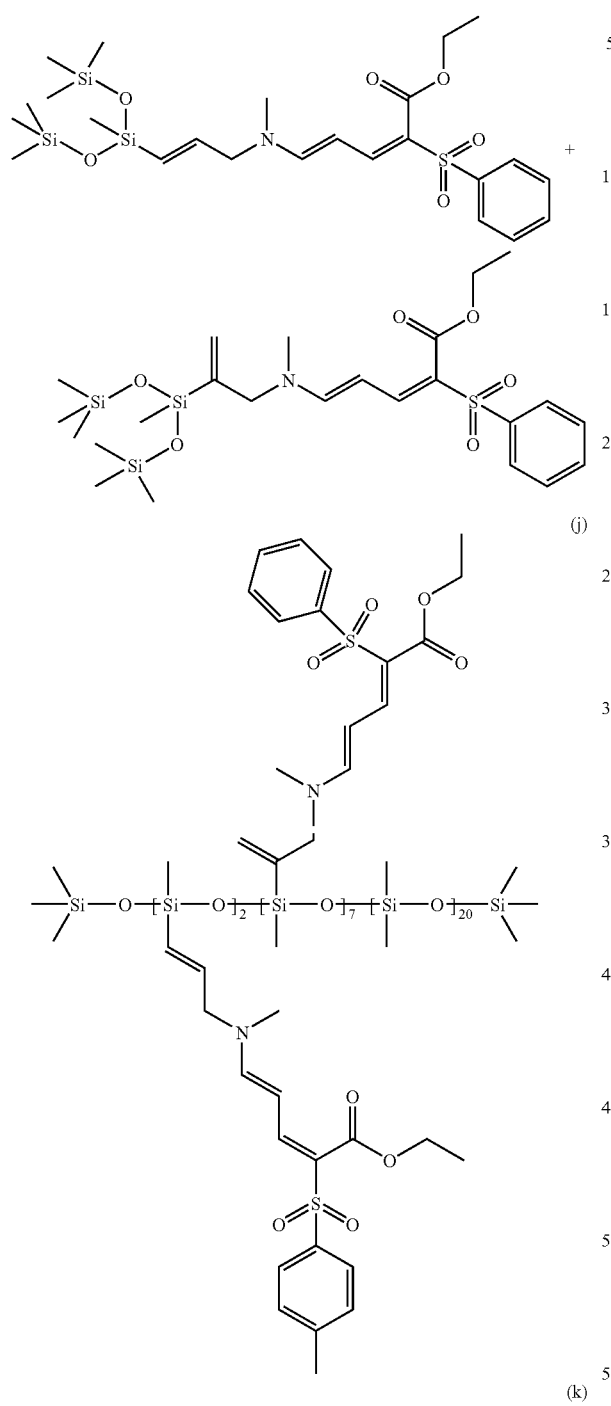

The derivatives of formula (1) may be prepared via a method described in U.S. Pat. Nos. 4,045,229 and 4,195,999 in accordance with the following reaction scheme:

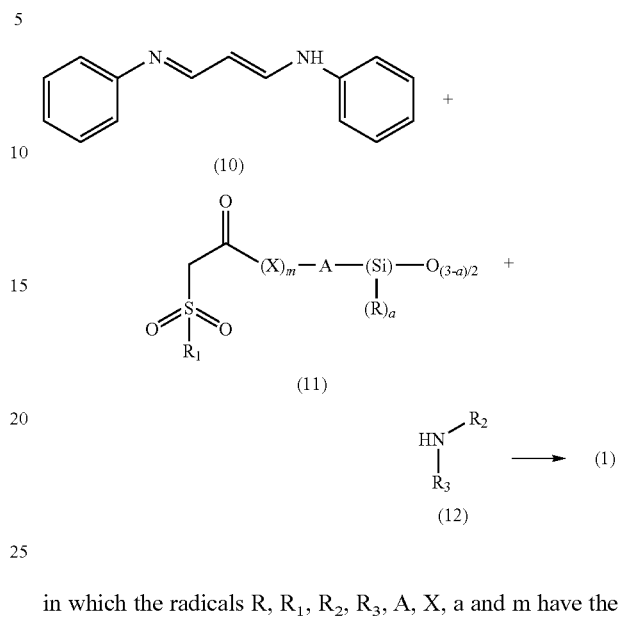

in which the radicals R, $R_1$, $R_2$, $R_3$, A, X, a and m have the definitions given in the above formulae.

The derivatives of formula (2) may be prepared via a method described in WO-A-00/20388 in accordance with the following reaction scheme:

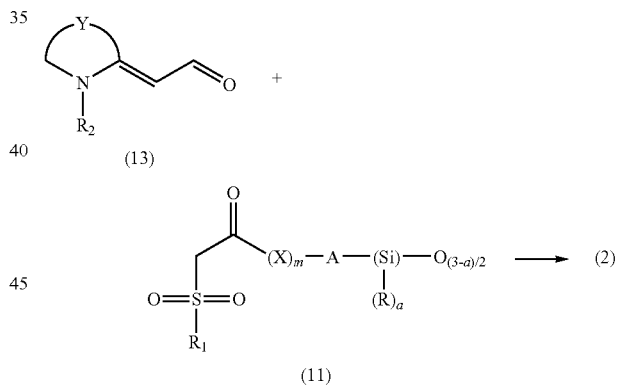

in which the radicals R, $R_1$, $R_2$, $R_3$, A, X, Y, a and m have the definitions given in the above formulae.

The derivatives of formula (3) may be prepared via a method described in U.S. Pat. Nos. 4,045,229 and 4,195,999 in accordance with the following reaction scheme:

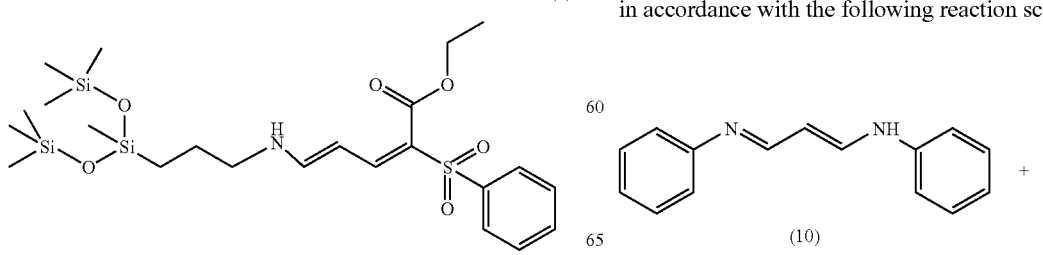

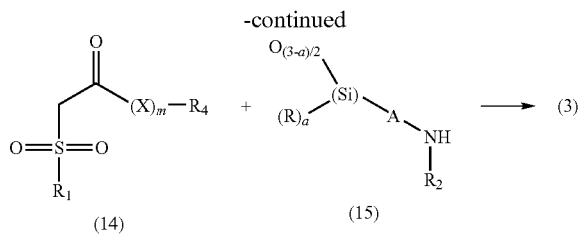

in which the radicals R, $R_1$, $R_2$, $R_4$, A, X, a and m have the definitions given in the above formulae.

The compounds of formula (11) may be obtained conventionally by carrying out a hydrosilylation reaction starting from a siloxane or silane derivative of formulae (7) to (8) in which, for example, all of the radicals (D) are hydrogen atoms, said derivative hereinafter being termed a SiH derivative, and an unsaturated derivative in accordance with the following reaction scheme:

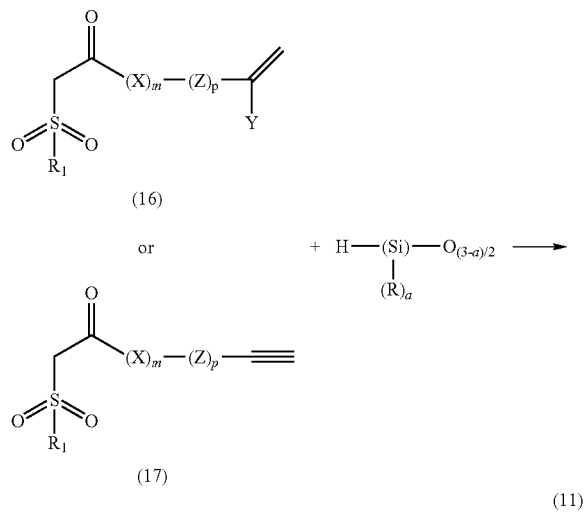

in which the radicals R, $R_1$, A, X, Y, Z, a, m and p have the definitions given in the above formulae.

The SiH groups may be present in the chain and/or at the chain ends. Said SiH derivatives are substances which are well known in the silicone industry and are generally commercially available. They have, for example, been described in U.S. Pat. Nos. 3,220,972, 3,697,473 and 4,340,709.

In the same manner, the derivatives of formula (15) may be obtained in accordance with the following reaction scheme:

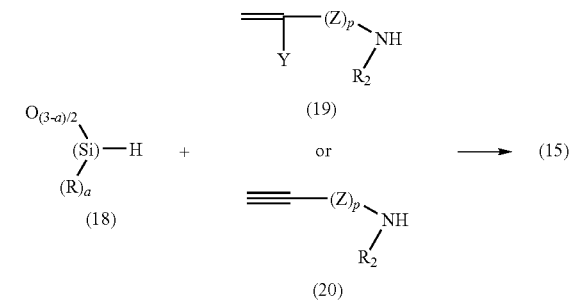

in which the radicals R, $R_2$, Y, Z, a and p have the definitions given in the above formulae.

The compositions of the invention may further contain other complementary organic or inorganic UV filters which are active in the UV-A and/or UV-B regions, which are hydrosoluble or liposoluble or even insoluble in cosmetic solvents in current use.

In particular, the complementary organic filters are selected from among anthranilates; cinnamic derivatives; salicylic derivatives, camphor derivatives; triazine derivatives other than those according to the invention, such as those described in U.S. Pat. No. 4,367,390, EP-A-0,863,145, EP-A-0,517,104, EP-A-0,570,838, EP-A-0,796,851, EP-A-0,775,698, EP-A-0,878,469, EP-A-0,933,376, EP-A-0,507,691, EP-A-0,507,692, EP-A-0,790,243, EP-A-0,944,624; benzophenone derivatives; β,β-diphenylacrylate derivatives; benzotriazole derivatives; benzalmalonate derivatives; benzimidazole derivatives; imidazolines; bis-benzoazolyl derivatives as described in EP-A-0,669,323 and U.S. Pat. No. 2,463,264; p-aminobenzoic acid (PABA) derivatives; methylene bis-(hydroxyphenyl benzotriazole) derivatives as described in U.S. Pat. Nos. 5,237,071, 5,166,355, GB-A-2,303,549, DE-A-197,26,184 and EP-A-0,893,119; polymer filters and silicone filters, such as those described in particular in WO-A-93/04665; dimers derived from α-alkylstyrene, such as those described in DE-A-1 985 5649; 4,4-diarylbutadienes, such as those described in EP-A-0,967,200, DE-A-1974 6654, DE-A-1975 5649, EP-A-1,008,586, EP-A-1,133,980 and EP-A-0,133,981, and mixtures thereof.

Exemplary complementary organic filters are those noted below with their INCI name:

Para-aminobenzoic acid derivatives:
PABA;
Ethyl PABA;
Ethyl Dihydroxypropyl PABA;
Ethylhexyl Dimethyl PABA, especially that marketed under the trademark "ESCALOL 507" by ISP;
Glyceryl PABA;
PEG-25 PABA marketed under the trademark "UVINUL P25" by BASF.

Salicylic derivatives:
Homosalate marketed under the trademark "Eusolex HMS" by Rona/EM Industries;
Ethylhexyl Salicylate marketed under the trademark "NEO HELIOPAN OS" by HAARMANN and REIMER;
Dipropyleneglycol Salicylate marketed under the trademark "DIPSAL" by SCHER;
TEA Salicylate, marketed under the trademark "NEO HELIOPAN TS" by HAARMANN and REIMER.

Cinnamic derivatives:
Ethylhexyl Methoxycinnamate, especially that marketed under the trademark "PARSOL MCX" by HOFFMANN LA ROCHE;
Isopropyl Methoxy cinnamate;
Isoamyl Methoxy cinnamate marketed under the trademark "NEO HELIOPAN E 1000" by HAARMANN and REIMER;
DEA Methoxycinnamate;
Diisopropyl Methylcinnamate;
Glyceryl Ethylhexanoate Dimethoxycinnamate;

β,β'-diphenylacrylate derivatives:
Octocrylene, especially that marketed under the trademark "UVINUL N539" by BASF;
Etocrylene, especially that marketed under the trademark "UVINUL N35" by BASF.

Benzophenone derivatives:
Benzophenone-1 marketed under the trademark "UVINUL 400" by BASF;
Benzophenone-2 marketed under the trademark "UVINUL D50" by BASF;

Benzophenone-3 or Oxybenzone, marketed under the trademark "UVINUL M40" by BASF;
Benzophenone-4 marketed under the trademark "UVINUL MS40" by BASF;
Benzophenone-5;
Benzophenone-6 marketed under the trademark "Helisorb 11" by Norquay;
Benzophenone-8 marketed under the trademark "SpectraSorb UV-24" by American Cyanamid;
Benzophenone-9 marketed under the trademark "UVINUL DS-49" by BASF;
Benzophenone-12;
Diethylamino Hydroxybenzoyl Hexyl Benzoate marketed under the trademark "UVINUL A PLUS" by BASF.
Benzylidene camphor derivatives:
3-Benzylidene camphor marketed under the trademark "MEXORYL SD" by CHIMEX;
4-Methylbenzylidene camphor marketed under the trademark "EUSOLEX 6300" by MERCK;
Benzylidene Camphor Sulfonic Acid marketed under the trademark "MEXORYL SL" by CHIMEX;
Camphor Benzalkonium Methosulfate marketed under the trademark "MEXORYL SO" by CHIMEX;
Terephthalylidene Dicamphor Sulfonic Acid marketed under the trademark "MEXORYL SX" by CHIMEX;
Polyacrylamidomethyl Benzylidene Camphor marketed under the trademark "MEXORYL SW" by CHIMEX.
Phenyl benzimidazole derivatives:
Phenylbenzimidazole Sulfonic Acid, especially that marketed under the trademark "EUSOLEX 232" by MERCK;
Disodium Phenyl Dibenzimidazole Tetra-sulfonate marketed under the trademark "NEO HELIOPAN AP" by HAARMANN and REIMER.
Triazine derivatives:
Bis-Ethylhexyloxyphenol Methoxyphenyl Triazine marketed under the trademark "TINOSORB S" by CIBA GEIGY;
Ethylhexyl triazone, especially that marketed under the trademark "UVINUL T150" by BASF;
Diethylhexyl Butamido Triazone marketed under the trademark "UVASORB HEB" by SIGMA 3V.
Phenyl benzotriazole derivatives:
Drometrizole Trisiloxane marketed under the trademark "Silatrizole" by RHODIA CHIMIE;
Methylene bis-Benzotriazolyl Tetramethylbutylphenol, marketed in the solid form under the trademark "MIXXIM BB/100" by FAIRMOUNT CHEMICAL or in the micronized form in aqueous dispersion under the trademark "TINOSORB M" by CIBA SPECIALTY CHEMICALS.
Anthranilic derivatives:
Menthyl anthranilate marketed under the trademark "NEO HELIOPAN MA" by HAARMANN and REIMER.
Imidazoline derivatives:
Ethylhexyl Dimethoxybenzylidene Dioxoimidazoline Propionate.
Benzalmalonate derivatives:
Polyorganosiloxanes with a benzalmalonate function such as Polysilicone-marketed under the trademark "PARSOL SLX" by HOFFMANN LA ROCHE.
4,4-diarylbutadiene derivatives:
1,1-dicarboxy (2,2'-dimethylpropyl)-4,4-diphenylbutadiene and mixtures thereof;
Benzoxazole derivatives:
2,4-bis-[5-1(dimethylpropyl)benzoxazol-2-yl-(4-phenyl) imino]-6-(2-ethylhexyl)imino-1,3,5-triazine marketed under the trademark Uvasorb K2A by Sigma 3V;
and mixtures thereof.

Preferred complementary organic UV filters are selected from among:
Ethylhexyl Salicylate;
Homosalate;
Ethylhexyl Methoxycinnamate;
Octocrylene;
Phenylbenzimidazole Sulfonic Acid;
Disodium Phenyl Dibenzimidazole Tetra-sulfonate;
Benzophenone-3;
Benzophenone-4;
Benzophenone-5;
n-Hexyl 2-(4-diethylamino-2-hydroxybenzoyl)benzoate;
4-Methylbenzylidene camphor;
Terephthalylidene Dicamphor Sulfonic Acid;
Anisotriazine;
Ethylhexyl triazone;
Diethylhexyl Butamido Triazone;
Methylene bis-Benzotriazolyl Tetramethylbutylphenol;
Drometrizole Trisiloxane;
Polysilicone-15;
1,1-Dicarboxy (2,2'-dimethylpropyl)-4,4-diphenylbutadiene;
2,4-Bis-[5-1-(dimethylpropyl)benzoxazol-2-yl-(4-phenyl)imino]-6-(2-ethylhexyl)imino-1,3,5-triazine; and mixtures thereof.

The complementary inorganic photoprotective agents are selected from among pigments, more preferably from among nanopigments (mean primary particle size: generally from 5 nm to 100 nm, preferably from 10 nm to 50 nm) of treated or untreated metal oxides such as nanopigments of titanium (amorphous or crystalline in the form of rutile and/or anatase), iron, zinc, zirconium or cerium oxide.

Treated nanopigments are pigments which have undergone one or more chemical, electronic, chemical-mechanical and/ or mechanical surface treatments with compounds such as those described, for example, in *Cosmetics & Toiletries,* February 1990, vol. 105, p 53-64, such as amino acids, beeswax, fatty acids, fatty alcohols, anionic surfactants, lecithins, sodium, potassium, zinc, iron or aluminum salts of fatty acids, metal alkoxides (titanium or aluminum), polyethylene, silicones, proteins (collagen, elastin), alkanolamines, oxides of silicon, metal oxides, sodium hexametaphosphate, alumina or glycerin.

More particularly, the treated nanopigments may be oxides of titanium treated with:
silica and alumina, such as "Microtitanium Dioxide MT 500 SA" and "Microtitanium Dioxide MT 100 SA" from TAYCA, and "Tioveil Fin", "Tioveil OP", "Tioveil MOTG" and "Tioveil IPM" from TIOXIDE;
alumina and aluminum stearate, such as "Microtitanium Dioxide MT 100 T" from TAYCA;
alumina and aluminum laurate, such as "Microtitanium Dioxide MT 100 S" from TAYCA;
iron oxides and iron stearate, such as "Microtitanium Dioxide MT 100 F" from TAYCA;
silica, alumina and silicone, such as "Microtitanium Dioxide MT 100 SAS", "Microtitanium Dioxide MT 600 SAS" and "Microtitanium Dioxide MT 500 SAS" from TAYCA;
sodium hexametaphosphate, such as "Microtitanium Dioxide MT 150 W" from TAYCA;
octyltrimethoxysilane, such as "T-805" from DEGUSSA;
alumina and stearic acid, such as "UVT-M160" from KEMIRA;
alumina and glycerin, such as "UVT-M212" from KEMIRA;
alumina and silicone, such as "UVT-M262" from KEMIRA.

Other titanium oxide nanopigments treated with a silicone are preferably $TiO_2$ treated with octyl trimethyl silane with a mean elementary particle size in the range 25 nm to 40 nm, such as that marketed under the trademark "T 805" by DEGUSSA SILICES, $TiO_2$ treated with a polydimethylsiloxane with a mean elementary particle size of 21 nm, such as that marketed under the trademark "70250 CARDRE UF TiO2SI3" by CARDRE, anatase/rutile $TiO_2$ treated with a polydimethylhydrogenosiloxane with a mean elementary particle size of 25 nm, such as that marketed under the trademark "MICRO TITANIUM DIOXYDE USP GRADE HYDROPHOBIC" by COLOR TECHNIQUES.

Examples of non-coated titanium oxide nanopigments are those marketed by TAYCA under the trademarks "MICROTITANIUM DIOXIDE MT 500 B" or "MICROTITANIUM DIOXIDE MT600 B", by DEGUSSA under the trademark "P 25", by WACKER under the trademark "Oxyde de titane transparent PW", by MIYOSHI KASEI under the trademark "UFTR", by TOMEN under the trademark "ITS" and by TIOXIDE under the trademark "TIOVEIL AQ".

Examples of non-coated zinc oxide nanopigments are:

those marketed under the trademark "Z-COTE" by SUNSMART;

those marketed under the trademark "NANOX" by ELEMENTIS;

those marketed under the trademark "NANOGARD WCD 2025" by NANOPHASE TECHNOLOGIES.

Examples of coated zinc oxide nanopigments are:

those marketed under the trademark "OXIDE ZINC CS-5" by Toshibi (ZnO coated with polymethylhydrogenosiloxane);

those marketed under the trademark "NANOGARD ZINC OXIDE FN" by NANOPHASE TECHNOLOGIES (in 40% dispersion in Finsolv TN, benzoate of $C_{12}$-$C_{15}$ alcohols);

those marketed under the trademark "DAITOPERSION ZN-30" and "DAITOPERSION ZN-50" by Daito (dispersions in cyclopolymethylsiloxane/oxyethylenated polydimethylsiloxane, containing 30% or 50% zinc nano-oxides coated with silica and polymethylhydrogenosiloxane);

those marketed under the trademark "NFD ULTRAFINE ZNO" by Daikin (ZnO coated with perfluoroalkyl phosphate and copolymer based on perfluoroalkylethyl in dispersion in cyclopentasiloxane);

those marketed under the trademark "SPD-Z1" by Shin-Etsu (ZnO coated with silicone-grafted acrylic polymer, dispersed in cyclodimethylsiloxane);

those marketed under the trademark "ESCALOL Z100" by ISP (alumina-treated ZnO dispersed in an ethylhexyl methoxycinnamate/PVP-hexadecene copolymer/methicone mixture);

those marketed under the trademark "FUJI ZNO-SMS-10" by Fuji Pigment (silica-coated ZnO and polymethylsilsesquioxane);

those marketed under the trademark "NANOX GEL TN" by Elementis (ZnO dispersed to 55% in benzoate of $C_{12}$-$C_{15}$ alcohols with hydroxystearic acid polycondensate).

Non-coated cerium oxide nanopigments are marketed under the trademark "COLLOIDAL CERIUM OXIDE" by RHONE POULENC.

Examples of non-coated iron oxide nanopigments are those marketed by ARNAUD under the trademarks "NANOGARD WCD 2002 (FE 45B)", "NANOGARD IRON FE 45 BL AQ", "NANOGARD FE 45R AQ", "NANOGARD WCD 2006 (FE 45R)", or by MITSUBISHI under the trademark "TY-220".

Examples of coated iron oxide nanopigments are those marketed by ARNAUD under the trademarks "NANOGARD WCD 2008 (FE 45B FN)", "NANOGARD WCD 2009 (FE 45B 556)", "NANOGARD FE 45 BL 345", "NANOGARD FE 45 BL", or by BASF under the trademark "OXYDE DE FER TRANSPARENT".

Mixtures of metal oxides are also exemplary, in particular titanium dioxide and cerium dioxide; an equal weight mixture of silica-coated titanium dioxide and silica-coated cerium dioxide is marketed by IKEDA under the trademark "SUNVEIL A", and a mixture of titanium dioxide and zinc dioxide coated with alumina, silica and silicone such as "M 261" marketed by KEMIRA or coated with alumina, silica and glycerin such as "M 211" marketed by KEMIRA.

The nanopigments may be introduced into the compositions of the invention as they are or in the form of a pigmenting paste, i.e., mixed with a dispersing agent as described, for example, in GB-A-2,206,339.

The additional photoprotective agents are generally present in the compositions of the invention in proportions of 0.01% to 20% by weight with respect to the total composition weight, preferably 0.1% to 10% by weight with respect to the total composition weight.

The compositions of the invention may also contain artificial skin tanning and/or browning agents (self-tanning agents), more particularly dihydroxyacetone (DHA). They are preferably present in a quantity of 0.1% to 10% by weight with respect to the total composition weight.

The compositions of the present invention may further comprise conventional cosmetic adjuvants, in particular selected from among fats, organic solvents, ionic or non-ionic, hydrophilic or lipophilic thickening agents, softeners, moisturizers, opacifying agents, stabilizers, emollients, silicones, anti-foaming agents, fragrances, preservatives, anionic, cationic, non-ionic, zwitterionic or amphoteric surfactants, active ingredients, fillers, polymers, propellants, alkalinizing or acidifying agents or any other ingredient which is normally used in the cosmetics and/or dermatological field.

The fats may be constituted by an oil or wax or a mixture thereof. The term "oil" means a compound which is liquid at ambient temperature. The term "wax" means a compound which is solid or substantially solid at ambient temperature, generally with a melting point of more than 35° C.

Oils which are exemplary include mineral oils (paraffin); vegetable oils (sweet almond oil, macadamia oil, blackcurrant seed oil, jojoba oil); synthetic oils such as perhydrosqualene, fatty alcohols, acids or esters (such as the benzoate of $C_{12}$-$C_{15}$ alcohols marketed under the trademark "Finsolv TN" by WITCO, octyl palmitate, isopropyl lanolate, triglycerides including those of capric/caprylic acid), oxyethylenated or oxypropylenated fatty esters and ethers; silicone or fluorinated oils (cycomethicone, polydimethylsiloxanes or PDMS), or polyalkylenes.

Waxy compounds which are exemplary include paraffin, carnauba wax, beeswax and hydrogenated castor oil.

Organic solvents which are exemplary include low alcohols and polyols which may be selected from glycols and glycol ethers such as ethylene glycol, propylene glycol, butylene glycol, dipropylene glycol or diethylene glycol.

Hydrophilic thickening agents which are exemplary include carboxyvinyl polymers such as carbopols (carbomers) and Pemulens (acrylate/C10-C30-alkylacrylate copolymer); polyacrylamides such as crosslinked copolymers marketed under the trademarks Sepigel 305 (CTFA name: polyacrylamide/C13-14 isoparaffin/Laureth 7) or Simulgel 600 (CTFA name: acrylamide/sodium acryloyldimethyltaurate copolymer/isohexadecane/polysorbate 80) from Seppic; polymers and copolymers of 2-acrylamido 2-methylpropane sulfonic acid, which may be crosslinked and/or neutralized, such as poly-(2-acrylamido 2-methylpropane sulfonic acid) marketed by Hoechst under the trademark "Hostacerin AMPS" (CTFA name: ammonium polyacryldimethyltauramide); cellulose derivatives such as hydroxyethylcellulose; polysaccharides and in particular gums such as xanthan gum; and mixtures thereof.

Lipophilic thickening agents which are exemplary include modified clays such as hectorite and its derivatives, such as products marketed under Bentone's trademarks.

Active ingredients which are exemplary include:
anti-pollution agents and/or radical scavengers;
depigmenting agents and/or propigmenting agents;
anti-glycation agents;
NO synthase inhibitors;
agents stimulating the synthesis of dermal or epidermal macromolecules and/or preventing their degradation;
agents stimulating the proliferation of fibroblasts;
agents stimulating the proliferation of keratinocytes;
myorelaxing agents;
tightening agents;
desquamating agents;
moisturizing agents;
anti-inflammatory agents;
agents acting on the energetic metabolism of cells;
insect-repelling agents;
antagonists for P or CRGP substances.

Of course, one skilled in this art will carefully select any complementary compounds indicated above and/or their quantities if used, such that the advantageous intrinsic properties of the compositions of the invention are not or are not substantially altered by the envisaged adjuncts.

The compositions of the invention may be prepared using techniques which are well known to one skilled in this art, in particular those suited for the preparation of oil-in-water or water-in-oil type emulsions. In particular, they may be in the form of an emulsion, which may be simple or complex (O/W, W/O, O/W/O or W/O/W), such as a cream or a milk, or in the form of a gel or a cream gel, or in the form of a lotion, a powder, a solid stick or possibly packaged as an aerosol and in the form of a foam or spray.

Preferably, the compositions of the invention are in the form of an oil-in-water or water-in-oil emulsion.

Emulsions generally contain at least one emulsification agent selected from among amphoteric, anionic, cationic or non-ionic emulsification agents, used alone or as a mixture. The emulsification agents are selected appropriately depending on the emulsion to be obtained (W/O or O/W).

Emulsifying surfactants which can be used to prepare W/O emulsions which may, for example, be cited include alkyl esters or ethers of sorbitan, glycerol or sugars; silicone surfactants such as dimethicone copolyols, such as the mixture of cyclomethicone and dimethicone copolyol marketed under the trademark "DC 5225 C" by Dow Corning, and alkyldimethicone copolyols such as Laurylmethicone copolyol marketed under the trademark "Dow Corning 5200 Formulation Aid" by Dow Corning; Cetyl dimethicone copolyol, such as that marketed under the trademark Abil EM 90R by Goldschmidt and the mixture of cetyl dimethicone copolyol, polyglycerol isostearate (4 moles) and hexyl laurate marketed under the trademark ABIL WE O9 by Goldschmidt. In addition, one or more co-emulsification agents may be added which, advantageously, may be selected from the group including polyol alkylated esters. Polyol alkylated esters which are exemplary include in particular glycerol and/or sorbitan esters, for example polyglycerol isostearate such as the product marketed under the trademark Isolan GI 34 by Goldschmidt, sorbitan isostearate, such as that marketed under the trademark Arlacel 987 by ICI, sorbitan isostearate and glycerol, such as the product marketed under the trademark Arlacel 986 by ICI, and mixtures thereof.

Examples of emulsification agents for O/W emulsions which are representative include non-ionic emulsification agents such as oxyalkylenated (more particularly polyoxyethylenated) esters of fatty acids and glycerol; oxyalkylenated esters of fatty acids and sorbitan; oxyalkylenated (oxyethylenated and/or oxypropylenated) esters of fatty acids; oxyalkylenated (oxyethylenated and/or oxypropylenated) ethers of fatty alcohols; sugar esters, such as sucrose stearate; ethers of fatty alcohol and sugar, in particular alkylpolyglucosides (APG) such as decylglucoside and lauryl glucoside marketed, for example, by Henkel under the respective trademarks Plantaren 2000 and Plantaren 1200, cetostearylglucoside, possibly as a mixture with cetostearyl alcohol marketed, for example, under the trademark Montanov 68 by Seppic, under the trademark Tegocare CG90 by Goldschmidt and under the trademark Emulgade KE3302 by Henkel, as well as arachidyl glucoside, for example in the form of a mixture of arachidic and behenic alcohol and arachidyl glucoside marketed under the trademark Montanov 202 by Seppic. In a particular embodiment of the invention, the mixture of alkyl polyglucoside as defined above with the corresponding fatty alcohol may be in the form of a self-emulsifying composition as described, for example, in WO-A-92/06778.

With an emulsion, the aqueous phase thereof may comprise a non-ionic vesicular dispersion prepared using known methods (Bangham, Standish and Watkins. *J. Mol. Biol.*, 13, 238 (1965), FR-A-2,315,991 and FR-A-2,416,008).

The compositions of the invention find application in a large number of treatments (whether regime or regimen), in particular cosmetic, of the skin, lips and hair, including the scalp, especially to protect and/or care for the skin, lips and/or hair and/or to make up the skin and/or lips.

The present invention also features the formulation of the compositions of the invention as defined above into products for the cosmetic treatment of the skin, lips, nails, hair, eyelashes, eyebrows and/or scalp, in particular care products and makeup products.

The cosmetic compositions of the invention may, for example, be administered as a care product and/or sun care product for the face and/or the body with a liquid to semi-liquid consistency, such as milks, creams with varying degrees of oiliness, gel creams or pastes. They may be packaged as an aerosol and in the form of a foam or spray.

The compositions of the invention in the form of vaporizable fluid lotions in accordance with the invention are applied to the skin or hair in the form of fine particles using pressurization devices. The devices of the invention are well known in the art and include non-aerosol pumps or atomizers, aerosol receptacles including a propellant, and aerosol pumps using compressed air as the propellant. These have been described in U.S. Pat. Nos. 4,077,441 and 4,850,517 (forming an integral part of the contents of the description).

The compositions packaged in aerosol form in accordance with the invention generally contain conventional propellants such as hydrofluorinated compounds, dichlorodifluoromethane, difluoroethane, dimethyl ether, isobutane, n-butane, propane or trichlorofluoromethane. They are preferably present in quantities of 15% to 50% by weight with respect to the total composition weight.

In another embodiment, the present invention features the administration of a compound of formula (1), (2) or (3) as defined above in a cosmetic or dermatological composition as a UV radiation filter.

19

In another embodiment, this invention features the administration of a compound of formula (1), (2) or (3) as defined above in a cosmetic composition as an agent for controlling the variation in skin color due to UV radiation.

In another embodiment, this invention features the use of a compound of formula (1), (2) or (3) as defined above as an agent for photostabilizing synthetic polymers such as plastic materials or glass, in particular spectacle lenses or contact lenses.

In order to further illustrate the present invention and the advantages thereof, the following specific examples are given, it being understood that same are intended only as illustrative and in nowise limitative. In said examples to follow, all parts and percentages are given by weight, unless otherwise indicated.

EXAMPLE 1

Synthesis of Compound (g) of Formula (3)(4)(7):
n=1, a=1, m=1, X=O, $R_1$=p-tolyl,
R=$R_2$=$R_4$=$R_6$=(B)=—$CH_3$, p=1, W=H,
Z=—$CH_2$—, r=0, s=1

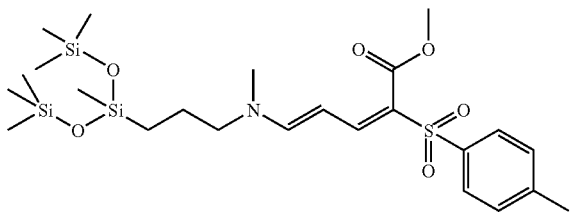

First Step: Preparation of methyl-5-[allyl(methyl)amino]-2-[(4-methylphenyl)sulfonyl]penta-2,4-dienoate 3-anilinoacrolein anil (1.2 g, 5.4×10$^{-3}$ mole) and methyl para-toluene sulfonylacetate (1.48 g, 6.48×10$^{-3}$ mole) were heated to 85°-90° C. in 5 ml of acetic anhydride for 2 hours, 30 minutes. The acetic anhydride was evaporated to dryness under reduced pressure. The oil obtained was taken up in 5 ml of ethanol. N-methyl allylamine (1.115 ml, 0.0117 mole) was added and the mixture was heated under reflux for 4 hours 30 minutes. The ethanol was evaporated to dryness under reduced pressure. The orangey-brown oil obtained was purified on a silica chromatographic column (eluent: EtOAc/heptane, 20:80 then a gradient to 30:70).

1.48 g of clean fractions (yield: 77%) of methyl-5-[allyl(methyl)amino]-2-[(4-methylphenyl)sulfonyl]penta-2,4-dienoate were recovered in the form of a pale yellow oil:
UV ($CH_2Cl_2$): $\lambda_{max}$=370 nm, $E_{1\%}$=1346
$\lambda_{max}$=356 nm (shoulder), $E_{1\%}$=1031.

Second Step: Synthesis of Compound of Example 1

0.371 g (1.67×10$^{-3}$ mole) of heptamethyltrisiloxane was added dropwise over 10 minutes to a solution of the preceding substance (0.508 g, 1.51×10$^{-3}$ mole) and catalyst (complex containing 3-3.5% by weight of Pt in cyclovinylmethylsiloxane from Hüls Petrarch, PC085: 100 µl) in 2 ml of dry toluene heated to 80° C. It was maintained at that temperature for 6 hours. The reaction mixture was concentrated. It was taken up in dichloromethane and that solution was passed over a bed of Celite. The pale yellow oil obtained was chromatographed on a silica column (eluent: heptane/EtOAc, 65:35). 0.45 g (yield: 53%) of clean fractions of the derivative of Example 1 was obtained in the form of a pale yellow oil which crystallized over time:
UV (Ethanol): $\lambda_{max}$=372 nm, $E_{1\%}$=1154
$\lambda_{max}$=356 nm (shoulder), $E_{1\%}$=773.

20

EXAMPLE 2

Synthesis of Compound (h) of Formula (3)(4)(7):
n=1, a=1, b=2, m=1, X=O, $R_1$=p-tolyl,
R=$R_2$=$R_4$=$R_6$=(B)=—$CH_3$, p=1, W=H,
Z=—$CH_2$—, r=s=6

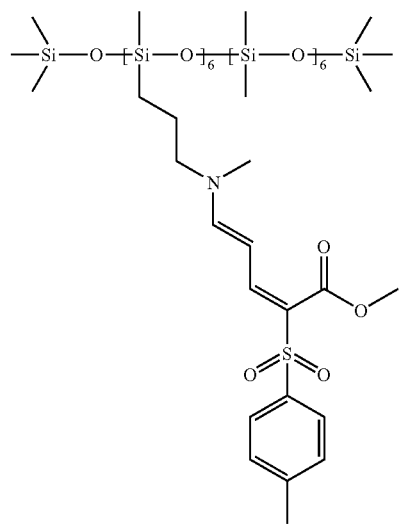

0.325 g (2 meq SiH) of methylhydro (50-55%) dimethylsiloxane (45-50%) copolymer (PS122.5 from Petrarch) was added dropwise over 10 minutes to a solution of methyl-5-[allyl(methyl)amino]-2-[(4-methylphenyl)sulfonyl]penta-2,4-dienoate (0.7 g, 2.1×10$^{-3}$ mole) obtained in the first step of Example 1 and catalyst (complex containing 3-3.5% by weight of Pt in cyclovinylmethylsiloxane from Hüls Petrarch, PC085: 80 µl) in 2 ml of dry toluene heated to 80° C. It was maintained at that temperature for 6 hours. The reaction mixture was concentrated. It was taken up in dichloromethane and that solution was passed over a bed of Celite. The pale yellow oil obtained was chromatographed on a silica column (eluent: $CH_2Cl_2$). 0.92 g of clean fractions of the derivative of Example 2 was obtained in the form of a viscous pale yellow oil:
UV (Ethanol): $\lambda_{max}$=371 nm, $E_{1\%}$=728.

EXAMPLE 3

Synthesis of Mixture of Compounds (i) of Formula (3)(5)(6)(7): n=1, a=1, m=1, X=O, $R_1$=-phenyl,
R=$R_2$=$R_6$=(B)=—$CH_3$, $R_4$=—$CH_2CH_3$, p=1,
Z=—$CH_2$—, r=0, s=1

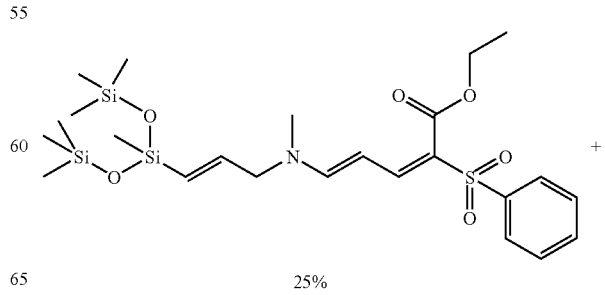

25%

-continued

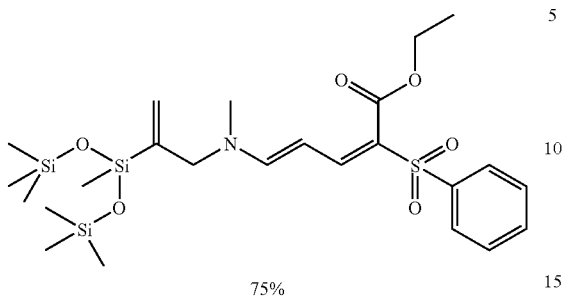

75%

First Step: Preparation of ethyl-5-[methyl(prop-2-ynyl)amino]-2-(phenylsulfonyl)penta-2,4-dienoate 3-anilinoacrolein anil (1.5 g, 6.75×10⁻³ mole) and ethyl phenyl sulfonylacetate (1.848 g, 8.1×10⁻³ mole) were heated to 85°-90° C. in 5 ml of acetic anhydride for 3 hours. The acetic anhydride was evaporated to dryness under reduced pressure. The oil obtained was taken up in 5 ml of ethanol. N-methyl propargylamine (1.22 ml, 0.0146 mole) was added and the mixture was heated under reflux for 5 hours. The ethanol was evaporated to dryness under reduced pressure. The orangey oil obtained was purified on a silica chromatographic column (eluent: EtOAc/heptane, 50:50 then a gradient to 30:70). 1.68 g of clean fractions (yield: 71%) of ethyl-5-[methyl(prop-2-ynyl)amino]-2-(phenylsulfonyl)penta-2,4-dienoate were recovered in the form of a pale yellow oil:

UV (CH$_2$Cl$_2$): $\lambda_{max}$=366 nm, E$_{1\%}$=1367

$\lambda_{max}$=358 nm (shoulder), E$_{1\%}$=1298.

Second Step: Synthesis of Compound of Example 3

0.413 g (1.86×10⁻³ mole) of heptamethyltrisiloxane was added dropwise over 10 minutes to a solution of the preceding substance (0.562 g, 1.69×10⁻³ mole) and catalyst (complex containing 3-3.5% by weight of Pt in cyclovinylmethylsiloxane from Hüls Petrarch PC085: 60 μl) in 2 ml of dry toluene heated to 80° C. It was maintained at that temperature for 6 hours. The reaction mixture was concentrated. It was taken up in dichloromethane and that solution was passed over a bed of Celite. The pale yellow oil obtained was chromatographed on a silica column (eluent: CH$_2$Cl$_2$). 0.35 g (yield: 37%) of clean fractions of the derivative of Example 3 was obtained in the form of an orangey-yellow oil which crystallized over time and in a ratio of 25:75, determined by ¹H NMR:

UV (Ethanol): $\lambda_{max}$=366 nm, E$_{1\%}$=1058

$\lambda_{max}$=356 nm (shoulder), E$_{1\%}$=705.

EXAMPLE 4

Synthesis of Mixture of Compounds (j) of Formula (3)(5)(6)(7): n=1, a=1, m=1, X=O, R$_1$=-phenyl, R=R$_2$=R$_6$=(B)=—CH$_3$, R$_4$=—CH$_2$CH$_3$, p=1, Z=—CH$_2$—, r=20, s=2+7

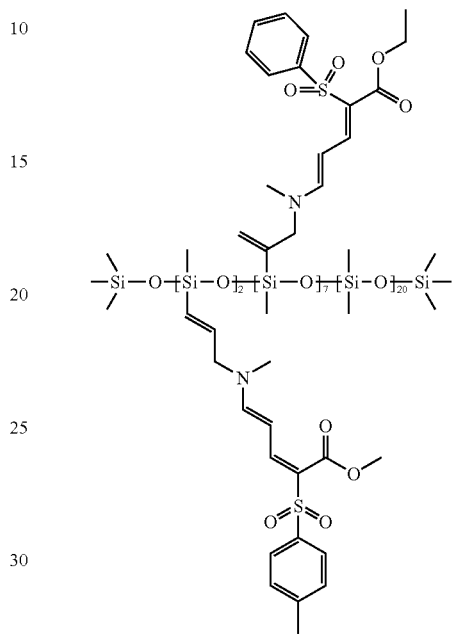

1.24 g (2.3 meq SiH) of methylhydro (30-35%) dimethylsiloxane (65-70%) copolymer (PDMS oil containing SiH, 628V14 from Rhone-Poulenc) were added dropwise over 10 minutes to a solution of ethyl-5-[methyl(prop-2-ynyl) amino]-2-(phenylsulfonyl)penta-2,4-dienoate (0.8 g, 2.41× 10⁻³ mole) obtained in the first step of Example 3 and catalyst (complex containing 3-3.5% by weight of Pt in cyclovinylmethylsiloxane from Hüls Petrarch, PC085: 110 μl) in 2 ml of dry toluene heated to 80° C. It was maintained at that temperature for 6 hours. The reaction mixture was concentrated. It was taken up in dichloromethane and that solution was passed over a bed of Celite. The pale yellow oil obtained was chromatographed on a silica column (eluent: CH$_2$Cl$_2$). 1.82 g of clean fractions of the derivative of Example 4 were obtained in the form of a viscous pale yellow oil:

UV (Ethanol): $\lambda_{max}$=366 nm, E$_{1\%}$=270.

FORMULATION EXAMPLES

EXAMPLE A

| | |
|---|---|
| Mixture of glycerol mono/distearate/ polyethyleneglycol stearate 100 OE (ARLACEL 165 FL- ICI) | 1.0 g |
| Cetyl alcohol | 0.5 g |
| Palm oil stearic acid (STEARINE TP-STEARINERIE DUBOIS) | 2.5 g |
| Polydimethylsiloxane (DOW CORNING 200 FLUID- DOW CORNING) | 0.5 g |
| Benzoate of C$_{12}$/C$_{15}$ alcohols (WITCONOL TN- WITCO) | 20 g |

-continued

| | |
|---|---|
| Compound of Example 1 | 2 g |
| Glycerin | 5.0 g |
| Hexadecyl alcohol phosphate, potassium salt (AMPHISOL K- HOFFMANN LA ROCHE) | 1.0 g |
| Polyacrylic acid (SYNTHALEN K- 3V) | 0.3 g |
| Hydroxypropylmethylcellusose (METHOCEL F4M- DOW CHEMICAL) | 0.1 g |
| Cyclopentadimethylsiloxane (DC245- DOW CORNING) | 2.0 g |
| Triethanolamine | 0.8 g |
| Preservatives | qs |
| Demineralized water | qs 100 g |

EXAMPLE B

| | |
|---|---|
| Mixture of cetylstearyl alcohol and oxyethylenated cetylstearyl alcohol, 33 OE (80/20) (SINNOWAX AO-HENKEL) | 7.0 g |
| Mixture of glycerol mono- and distearate (CERASYNT SD-V from ISP) | 2.0 g |
| Cetyl alcohol | 1.5 g |
| Polydimethylsiloxane (DOW CORNING 200 FLUID- DOW CORNING) | 1.5 g |
| Benzoate of $C_{12}/C_{15}$ alcohols (WITCONOL TN- WITCO) | 8.0 g |
| Vaseline oil | 10.0 g |
| Compound of Example 2 | 2.0 g |
| Glycerin | 10.0 g |
| Preservatives | qs |
| Demineralized water | qs 100 g |

Each patent, patent application, publication, text and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A silane, siloxane or polysiloxane merocyanine sulfone compound selected from the group consisting of those of the formulae (1), (2) and (3) below:

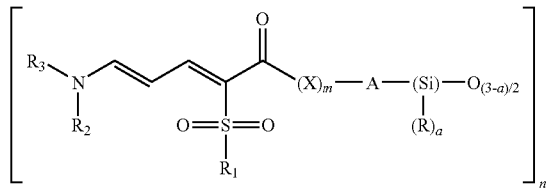

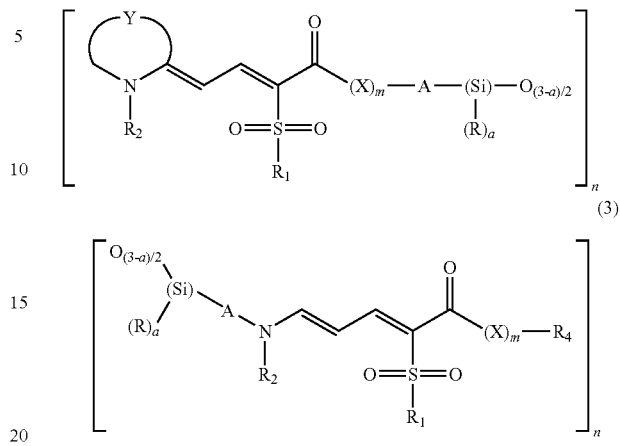

in which:

$m = 0$ or 1;

X is —O—, —$NR_5$—, —$SO_2NH$—, wherein $R_5$ is hydrogen or a $C_1$-$C_5$ alkyl radical;

Y is a divalent $C_1$-$C_5$ alkyl radical optionally substituted with $C_1$-$C_4$ alkyl radicals and/or containing —O—, —S— atoms or with a —$NR_1$ group;

the radicals R, which may be identical or different, are each a linear or branched and optionally halogenated $C_1$-$C_{20}$ alkyl radical, a $C_6$-$C_{12}$ aryl radical or a $C_1$-$C_{10}$ alkoxy radical;

$a = 0$ to 3;

$R_1$ is a linear or branched and optionally halogenated $C_1$-$C_{20}$ alkyl radical or a $C_6$-$C_{12}$ aryl radical;

$R_2$ and $R_3$, which may be identical or different, are each H, a $C_1$-$C_{24}$ alkyl radical, a $C_3$-$C_{10}$ cycloalkyl radical or a $C_6$-$C_{20}$ aryl radical optionally substituted with alkyl or alkoxy radicals, with the proviso that $R_2$ and $R_3$ may together form, with the nitrogen atom from which they depend, a $C_4$-$C_6$ cycle optionally interrupted by oxygen atoms or —NH—, and with the further proviso that $R_2$ and $R_3$ cannot each be a hydrogen atom;

A is a divalent radical selected from among methylene, ethylene or a group having one of the formulae (4), (5) or (6) below:

in which:

Z is a linear or branched, saturated or unsaturated $C_1$-$C_6$ alkylene radical optionally substituted with a hydroxyl radical, or a linear or branched, saturated or unsaturated $C_1$-$C_8$ alkyl radical;

W is a hydrogen atom, a hydroxyl radical or a linear or branched, saturated or unsaturated $C_1$-$C_8$ alkyl radical;

p is 0 or 1;

n=1 to 4 and when n=2, $R_1$, $R_2$, $R_3$ or $R_4$ is a divalent alkyl radical or $R_2$ and $R_3$ may together form with the nitrogen atom from which they depend, a $C_4$-$C_6$ cycle optionally interrupted by oxygen atoms or —NH—.

2. The silane, siloxane or polysiloxane merocyanine sulfone compound as defined by claim 1, having the formula (1).

3. The silane, siloxane or polysiloxane merocyanine sulfone compound as defined by claim 1, having the formula (2).

4. The silane, siloxane or polysiloxane merocyanine sulfone compound as defined by claim 1, having the formula (3).

5. The silane, siloxane or polysiloxane merocyanine sulfone compound as defined by claim 2, wherein the radical —(Si)(R)$_a$(O)$_{(3-a)/2}$ has one of formulae (7), (8) or (9) below:

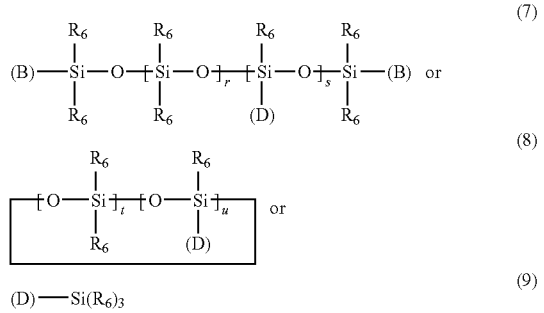

in which:
(D) is a linkage from the silicone chain and group A of the chromophores of formulae (1) to (3);
the radicals $R_6$, which may be identical or different, are each selected from among linear or branched $C_1$-$C_{30}$ alkyl, phenyl, 3,3,3-trifluoropropyl and trimethylsilyloxy radicals, at least 80% by number of the radicals $R_6$ being methyl;
the radicals (B), which may be identical or different, are each selected from among radicals $R_6$ and radical A;
r is a whole number in the range 0 to 200 inclusive and s is a whole number in the range 0 to 50 inclusive, and if s=0, at least one of the two symbols (B) designates A;
u is a whole number in the range 1 to 10 inclusive and t is a whole number in the range 0 to 10 inclusive, with the proviso that t+u is 3 or more.

6. The silane, siloxane or polysiloxane merocyanine sulfone compound as defined by claim 3, wherein the radical —(Si)(R)$_a$(O)$_{(3-a)/2}$ has one of formulae (7), (8) or (9) below:

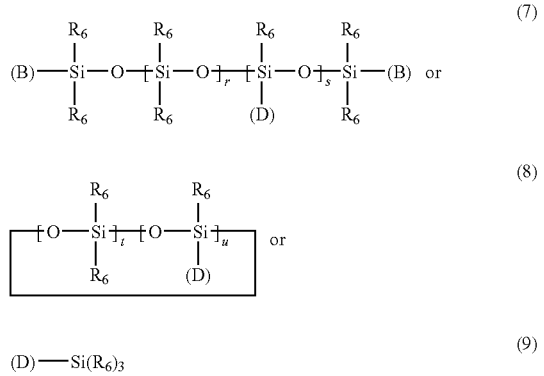

in which:
(D) is a linkage from the silicone chain and group A of the chromophores of formulae (1) to (3);
the radicals $R_6$, which may be identical or different, are each selected from among linear or branched $C_1$-$C_{30}$ alkyl, phenyl, 3,3,3-trifluoropropyl and trimethylsilyloxy radicals, at least 80% by number of the radicals $R_6$ being methyl;
the radicals (B), which may be identical or different, are each selected from among radicals $R_6$ and radical A;
is a whole number in the range 0 to 200 inclusive and s is a whole number in the range 0 to 50 inclusive, and if s=0, at least one of the two symbols (B) designates A;
u is a whole number in the range 1 to 10 inclusive and t is a whole number in the range 0 to 10 inclusive, with the proviso that t+u is 3 or more.

7. The silane, siloxane or polysiloxane merocyanine sulfone compound as defined by claim 4, wherein the radical —(Si)(R)$_a$(O)$_{(3-a)/2}$ has one of formulae (7), (8) or (9) below:

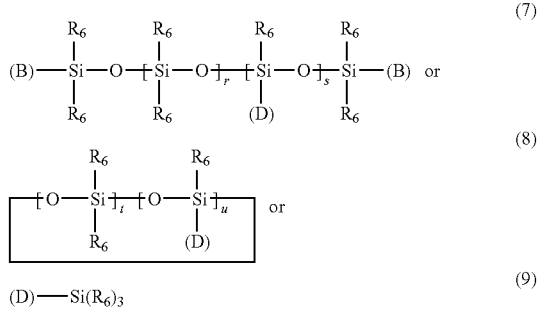

in which:
(D) is a linkage from the silicone chain and group A of the chromophores of formulae (1) to (3);
the radicals $R_6$, which may be identical or different, are each selected from among linear or branched $C_1$-$C_{30}$ alkyl, phenyl, 3,3,3-trifluoropropyl and trimethylsilyloxy radicals, at least 80% by number of the radicals $R_6$ being methyl;
the radicals (B), which may be identical or different, are each selected from among radicals $R_6$ and radical A;
r is a whole number in the range 0 to 200 inclusive and s is a whole number in the range 0 to 50 inclusive, and if s=0, at least one of the two symbols (B) designates A;
u is a whole number in the range 1 to 10 inclusive and t is a whole number in the range 0 to 10 inclusive, with the proviso that t+u is 3 or more.

8. The silane, siloxane or polysiloxane merocyanine sulfone compound as defined by claim 5, wherein the radical —(Si)(R)$_a$(O)$_{(3-a)/2}$ has the formulae (7) and either or both of $R_6$ and B is methyl.

9. The silane, siloxane or polysiloxane merocyanine sulfone compound as defined by claim 5, wherein the radical —(Si)(R)$_a$(O)$_{(3-a)/2}$ has the formulae (8) and either or both of $R_6$ and B is methyl.

10. The silane, siloxane or polysiloxane merocyanine sulfone compound as defined by claim 1, selected from the group consisting of those of the formulae (a) to (e) below:

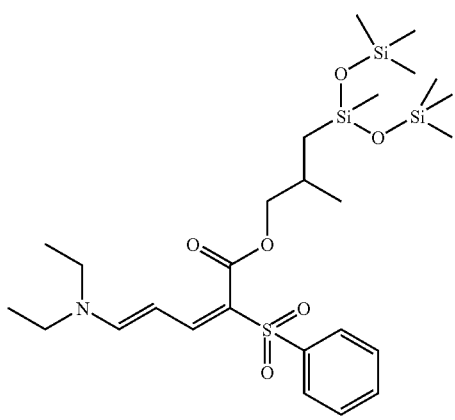
(a)
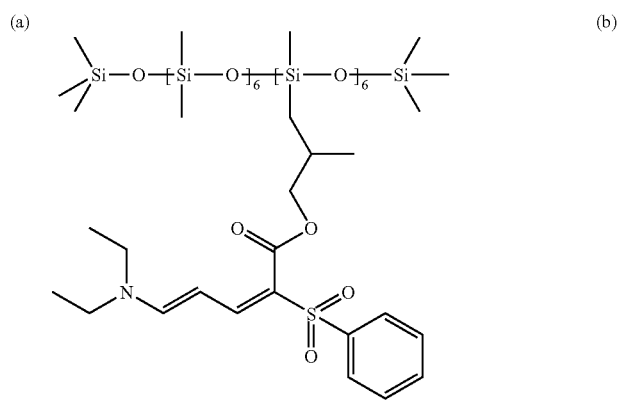
(b)
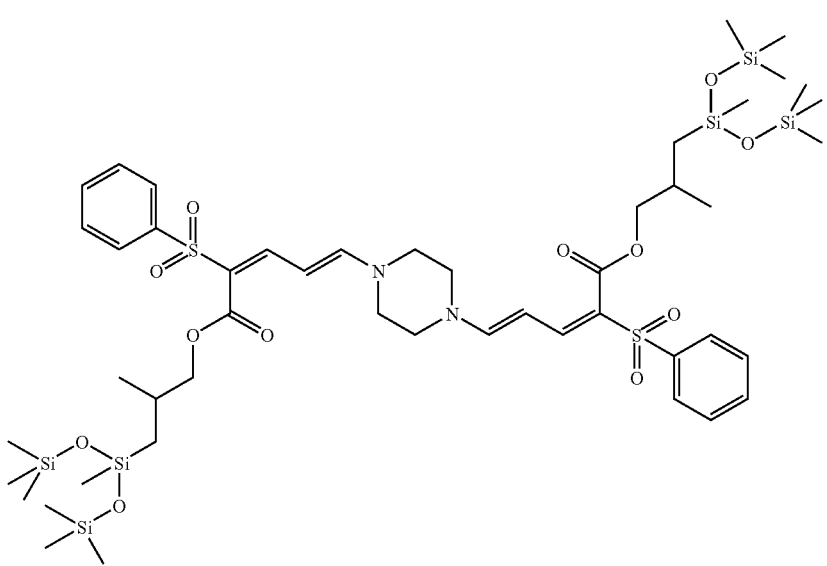
(c)
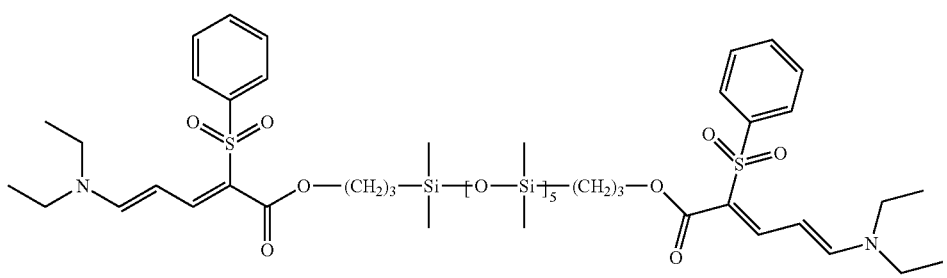
(d)

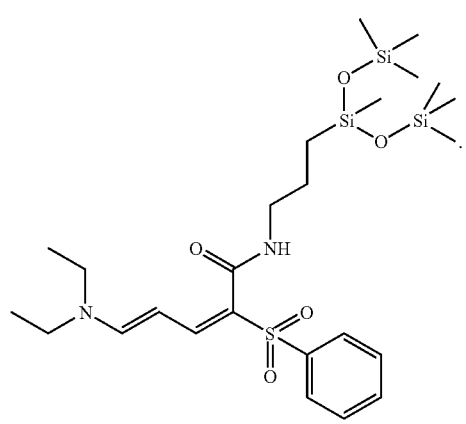
(e)
11. The silane, siloxane or polysiloxane merocyanine sulfone compound as defined by claim 1, comprising a mixture of compounds (f):
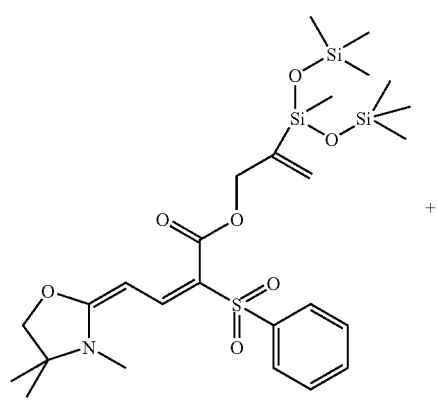
(f)
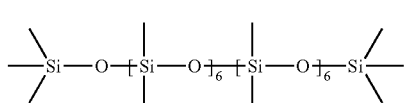
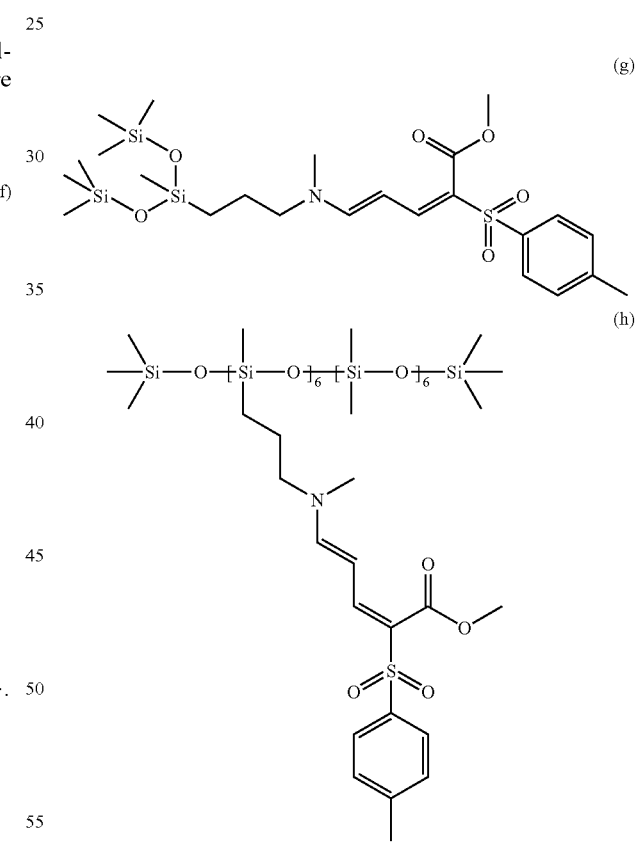
12. The silane, siloxane or polysiloxane merocyanine sulfone compound as defined by claim 1, selected from the group consisting of those of the formulae (g) to (k) below:

-continued

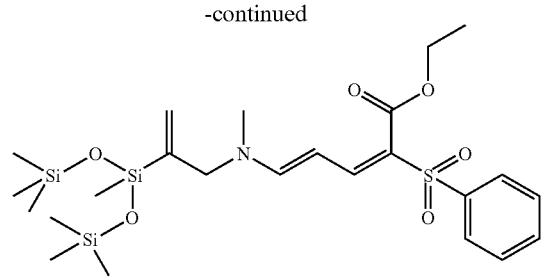

(j)

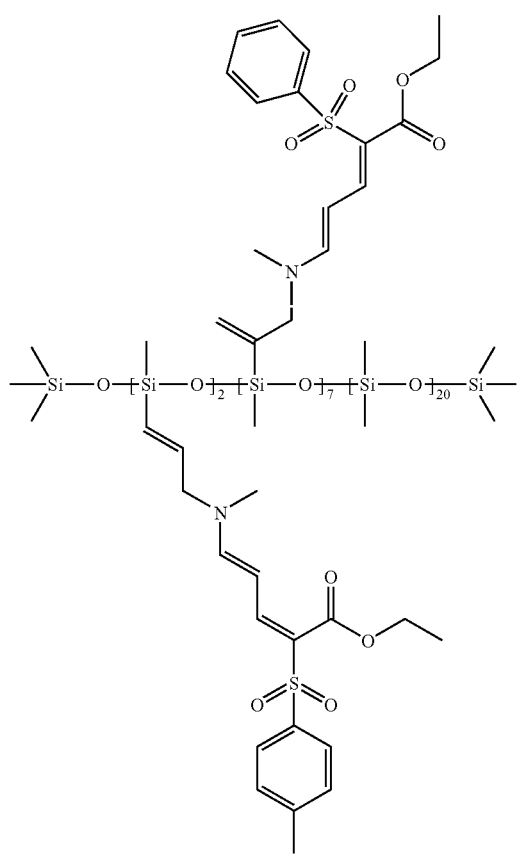

(k)

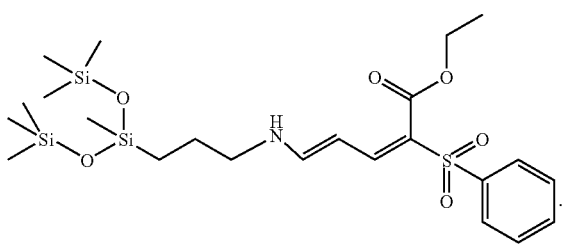

13. A topically applicable UV-photoprotecting cosmetic/dermatological composition comprising a thus effective amount of at least one silane, siloxane or polysiloxane merocyanine sulfone compound as defined by claim 1, formulated into a topically applicable, physiologically acceptable medium therefor.

14. The UV-photoprotecting cosmetic/dermatological composition as defined by claim 13, said at least one silane, siloxane or polysiloxane merocyanine sulfone compound comprising from 0.01% to 20% by weight thereof.

15. The UV-photoprotecting cosmetic/dermatological composition as defined by claim 13, said at least one silane, siloxane or polysiloxane merocyanine sulfone compound comprising from 0.1% to 10% by weight thereof.

16. The UV-photoprotecting cosmetic/dermatological composition as defined by claim 13, further comprising at least one other organic and/or inorganic UV-A and/or UV-B photoprotecting agent hydrosoluble, liposoluble or insoluble in conventional cosmetic solvents.

17. The UV-photoprotecting cosmetic/dermatological composition as defined by claim 16, comprising at least one organic photoprotective agent selected from the group consisting of anthranilates; cinnamic derivatives; salicylic derivatives; camphor derivatives; benzophenone derivatives; β,β-diphenylacrylate derivatives; triazine derivatives; benzotriazole derivatives; benzalmalonate derivatives; benzimidazole derivatives; imidazolines; bis-benzoazolyl derivatives; p-aminobenzoic acid (PABA) derivatives; methylene bis-(hydroxyphenyl benzotriazole) derivatives; benzoxazole derivatives; polymer filters and silicone filters; dimers derived from α-alkylstyrene; 4,4-diarylbutadienes and mixtures thereof.

18. The UV-photoprotecting cosmetic/dermatological composition as defined by claim 17, comprising at least one organic photoprotective agent selected from the group consisting of:
Ethylhexyl Salicylate;
Homosalate;
Ethylhexyl Methoxycinnamate;
Octocrylene;
Phenylbenzimidazole Sulfonic Acid;
Disodium Phenyl Dibenzimidazole Tetra-sulfonate;
Benzophenone-3;
Benzophenone-4;
Benzophenone-5;
Diethylamino Hydroxybenzoyl Hexyl Benzoate;
4-Methylbenzylidene camphor;
Terephthalylidene Dicamphor Sulfonic Acid;
Bis-Ethylhexyloxyphenol Methoxyphenyl Triazine;
Ethylhexyl Triazone;
Diethylhexyl Butamido Triazone;
Methylene bis-Benzotriazolyl Tetramethylbutylphenol;
Drometrizole Trisiloxane;
Polysilicone-15;
1,1-Dicarboxy (2,2'-dimethylpropyl)-4,4-diphenylbutadiene;
2,4-Bis-[5-1(dimethylpropyl)benzoxazol-2-yl-(4-phenyl)imino]-6-(2-ethylhexyl)imino-1,3,5-triazine;
and mixtures thereof.

19. The UV-photoprotecting cosmetic/dermatological composition as defined by claim 16, comprising at least one inorganic photoprotective agents selected from the group consisting of treated or untreated pigments or nanopigments of metal oxides.

20. The UV-photoprotecting cosmetic/dermatological composition as defined by claim 19, comprising treated or untreated pigments or nanopigments of the oxides of titanium, zinc, iron, zirconium, cerium and mixtures thereof.

21. The UV-photoprotecting cosmetic/dermatological composition as defined by claim 13, further comprising at least one artificial skin tanning and/or browning agent.

22. The UV-photoprotecting cosmetic/dermatological composition as defined by claim 13, further comprising at least one adjuvant selected from the group consisting of fats, organic solvents, ionic or non-ionic, hydrophilic or lipophilic thickening agents, softeners, moisturizers, opacifying agents, stabilizers, emollients, silicones, anti-foaming agents, fragrances, preservatives, anionic, cationic, non-ionic, zwitterionic or amphoteric surfactants, active ingredients, fillers, polymers, propellants, alkalinizing or acidifying agents and mixtures thereof.

23. The UV-photoprotecting cosmetic/dermatological composition as defined by claim 13, formulated as a cream, milk, gel, lotion, powder, paste, solid stick, foam or spray.

24. The UV-photoprotecting cosmetic/dermatological composition as defined by claim 13, formulated as an emulsion.

25. The UV-photoprotecting cosmetic/dermatological composition as defined by claim 13, formulated as a makeup.

26. A regime or regimen for photoprotecting the skin, lips, nails, hair, eyelashes, eyebrows and/or scalp against the damaging effects of UV radiation, comprising topically applying thereon a thus effective amount of the cosmetic/dermatological composition as defined by claim 13.

27. A regime or regimen for controlling the variation in skin color due to UV radiation, comprising topically applying thereon a thus effective amount of the cosmetic/dermatological composition as defined by claim 13.

28. A plastic, glass, spectacle lens or contact lens containing a photostabilizing amount of a silane, siloxane or polysiloxane merocyanine sulfone compound as defined by claim 1.

* * * * *